US012761200B2

(12) United States Patent
Yoshimine et al.

(10) Patent No.: US 12,761,200 B2
(45) Date of Patent: Oct. 13, 2026

(54) MANAGEMENT APPARATUS, MANAGEMENT METHOD, AND NON-TRANSITORY COMPUTER READABLE MEDIUM

(71) Applicant: Asahi Kasei Microdevices Corporation, Tokyo (JP)

(72) Inventors: Toshikazu Yoshimine, Tokyo (JP); Takaaki Furuya, Tokyo (JP); Keiichiro Kuwata, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 6 days.

(21) Appl. No.: 19/080,908

(22) Filed: Mar. 16, 2025

(65) Prior Publication Data

US 2025/0290908 A1 Sep. 18, 2025

(30) Foreign Application Priority Data

Mar. 18, 2024 (JP) ................................ 2024-042028
Jan. 30, 2025 (JP) ................................ 2025-013433

(51) Int. Cl.
*G01N 33/00* (2006.01)

(52) U.S. Cl.
CPC ..... *G01N 33/0073* (2013.01); *G01N 33/0006* (2013.01); *G01N 33/0031* (2013.01); *G01N 33/0063* (2013.01)

(58) Field of Classification Search
CPC ..... A61B 5/1117; A61B 5/7435; A61B 5/747; A61B 5/749; A61G 7/018; G08B 26/008; H04W 4/029; H04W 4/80
See application file for complete search history.

(56) References Cited

U.S. PATENT DOCUMENTS 4,569,223 A 2/1986 Huebner
2014/0278144 A1* 9/2014 Risk .................... G01D 18/008 702/24
2021/0204834 A1* 7/2021 Jameson ............... A61B 5/097
(Continued)

FOREIGN PATENT DOCUMENTS

JP S49105595 A 10/1974
JP H03107724 A 5/1991
(Continued)

*Primary Examiner* — Omer S Khan

(57) ABSTRACT

A management apparatus comprises: an acquisition unit that acquires first measurement information from a plurality of first sensors configured to measure a physical quantity related to environment in each of a plurality of areas, and acquires second measurement information from at least one second sensor configured to be mounted on at least one mobile object and to a measure physical quantity related to environment in each of the plurality of areas; an identification unit that identifies an abnormal area, where the physical quantity shows an abnormal value, based on each of the first measurement information and the second measurement information; and an authentication unit that authenticates that consistency between the first measurement information and the second measurement information is high when an abnormal area identified unit based on the first measurement information is an area identical to an abnormal area identified based on the second measurement information.

13 Claims, 8 Drawing Sheets

(56) References Cited

U.S. PATENT DOCUMENTS

| | | | | |
|---|---|---|---|---|
| 2023/0119608 | A1 | 4/2023 | Gains | |
| 2023/0324430 | A1* | 10/2023 | Reed | G01M 3/202 73/170.11 |
| 2024/0339021 | A1* | 10/2024 | Cooper | G08B 29/185 |

FOREIGN PATENT DOCUMENTS

| | | | |
|---|---|---|---|
| JP | 2007279887 | A | 10/2007 |
| JP | 2017194362 | A | 10/2017 |
| JP | 2018112485 | A | 7/2018 |
| JP | 2023141231 | A | 10/2023 |

* cited by examiner

10

MANAGEMENT APPARATUS, MANAGEMENT METHOD, AND NON-TRANSITORY COMPUTER READABLE MEDIUM

The contents of the following patent application(s) are incorporated herein by reference:

NO. 2024-042028 filed in JP on Mar. 18, 2024

NO. 2025-013433 filed in JP on Jan. 30, 2025.

BACKGROUND

1. Technical Field

The present invention relates to a management apparatus, a management method, and a non-transitory computer readable medium.

2. Related Art

In Patent Document 1, a system is disclosed for estimating how gases in the atmosphere are distributed.

PRIOR ART DOCUMENTS

Patent Documents

Patent Document 1: International Publication No. 2022/077119

DESCRIPTION OF EXEMPLARY EMBODIMENTS

Hereinafter, embodiments of the present invention will be described. However, the following embodiments are not for limiting the invention according to the claims. In addition, not all of the combinations of features described in the embodiments are essential to the solution of the invention.

Figure 1:
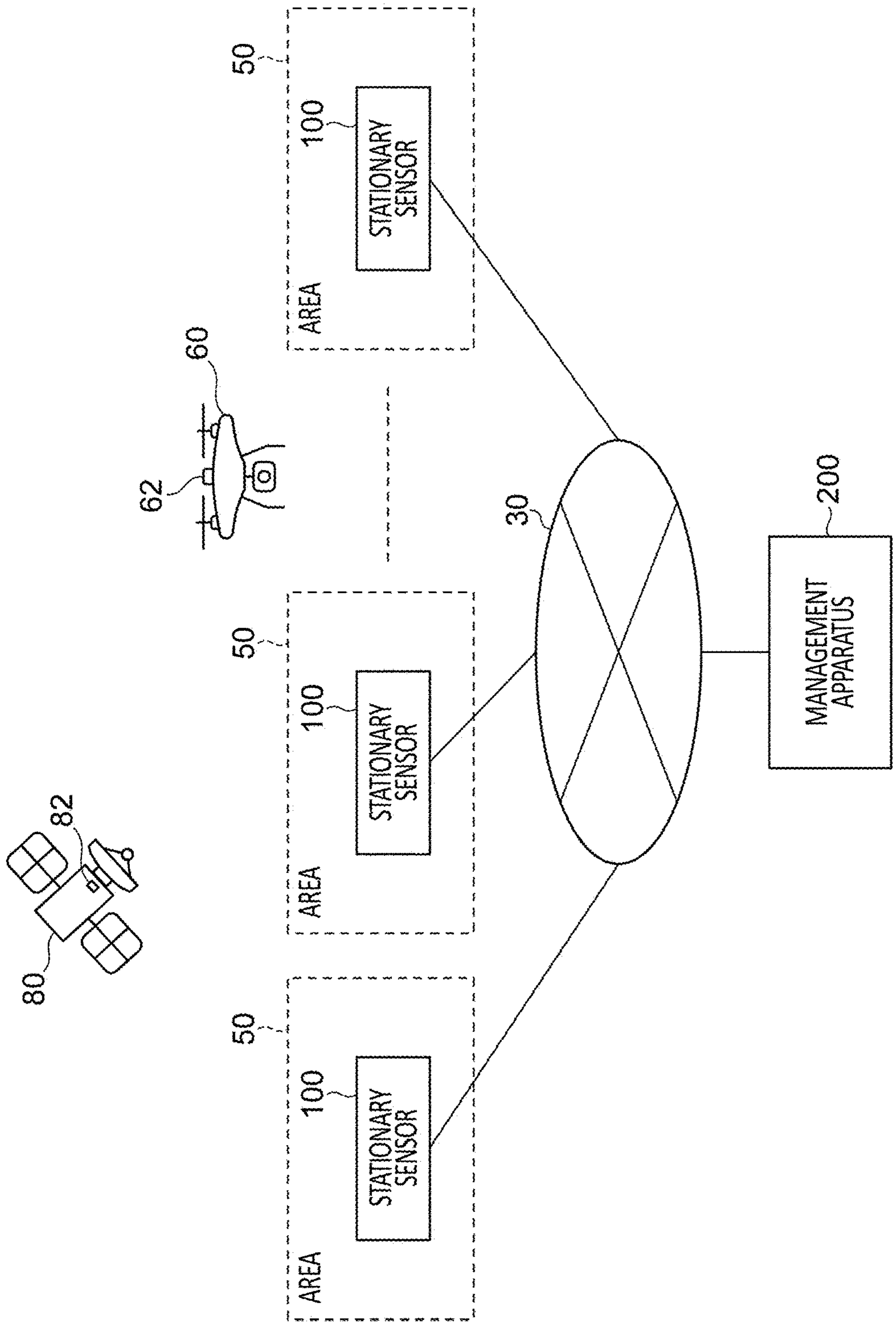
FIG. 1 shows an example of an overall configuration of a management system according to the present embodiment.

FIG. 1 shows an example of an overall configuration of a management system 10 according to the present embodiment. The management system 10 includes a plurality of stationary sensors 100, a UAV60, an artificial satellite 80 and a management apparatus 200. The management apparatus 200 may be a computer including a CPU and a memory, and the CPU may perform various functions by performing various programs stored in the memory. The stationary sensor 100, the UAV 60, the artificial satellite 80 and the management apparatus 200 communicates to each other via a network 30.

Each of the plurality of stationary sensors 100 is arranged in each of the plurality of areas 50 to be monitored. The plurality of areas 50 may be, for example, areas that may have target objects to be measured by the stationary sensor 100 existed therein. The plurality of areas 50 may overlap in some regions. The stationary sensor 100 is an example of a first sensor.

The stationary sensor 100 measures a physical quantity related to the environment in an area 50. The stationary sensor 100 may measure at least one of a gas concentration, dust amount, temperature, humidity, noise, illumination, vibration, electromagnetic waves, X-ray dose, radiation dose, wind direction, wind speed, air pressure, rainfall, solar radiation and ozone concentration to be measured in the area 50. Each physical quantity may be associated with measuring time and position coordinates.

For example, the plurality of areas 50 are pipelines and the stationary sensor 100 may be a gas sensor that detects a gas leakage of the gas passing through the pipelines. When the stationary sensor 100 is a gas sensor, a gas concentration of the gas to be measured may be measured according to a non-dispersive infrared absorption method, a Tunable Diode Laser Absorption Spectroscopy (TDLAS) method, a Differential Absorption LiDAR (DIAL) method, a Time Correlated Single Photon Counting (TCSPC) method, a photoacoustic method, a semiconductor method, a solid electrolyte method, a thermal conduction method, an acoustic wave method, an optical gas imaging method, or a capacitance method. The gas to be measured may be carbon dioxide, water, or oxygen. The gas to be measured may be combustible gases such as methane, propane, ethanol, hydrogen, ethylene, or MCH (methylcyclohexane). The gas to be measured may toxic gas such as carbon monoxide, hydrogen sulfide, formaldehyde, and ammonia. The gas to be measured may be greenhouse gas such as carbon dioxide, nitrous oxide, and refrigerant gas.

The stationary sensor 100 may be a dust sensor, a temperature/humidity sensor, a noise sensor, an illumination sensor, a vibration sensor, an electromagnetic wave meter, an X-ray meter, a radiation meter, a LiDAR (Light Detection And Ranging), a radar, a visible light imager, an infrared light imager, an air pressure sensor, an air flow tester or the like. The stationary sensor 100 may also include a watch and a position sensor.

An unmanned aerial vehicle (UAV) 60 is an example of a mobile object. The mobile object is a concept that includes a flight vehicle moving in the air, a vehicle moving on the ground, a ship moving on water, or the like. The flight vehicle moving in the air is a concept including the UAV, and another aircraft, airship, helicopter, and the like moving in the air. The UAV 60 includes a sensor 62. The sensor 62 is an example of a second sensor. The functions of the sensor 62 and a sensor 82 may be identical to that of the stationary sensor 100. The sensor 62 may be an identical sensor to the stationary sensor 100. That is, the UAV 60 may have a sensor identical to the stationary sensor 100 as the sensor 62 mounted thereon. The unmanned aerial vehicle (UAV) 60 may also include a watch and a position sensor.

The artificial satellite 80 is an example of a mobile object. The artificial satellite 80 includes a sensor 82. The sensor 82 is an example of the second sensor. The sensor 82 may measure a physical quantity identical to the physical quantity measured by the stationary sensor 100. The sensor 82 may be a gaseous component observation sensor such as an OMI (Ozone Monitoring Instrument) sensor. The sensor 82 may be a passive sensor that observes visible light, infrared light, or microwaves or the like reflected or emitted from the ground, ocean, atmosphere or the like or it may be an active sensor that directs electromagnetic waves toward an observation target and observes their reflected waves. The artificial satellite 80 may also include a watch and a position sensor.

The management apparatus 200 may collect measurement information based on the measurement data measured by the plurality of stationary sensors 100, the sensor 62 of the UAV 60 and the sensor 82 of the artificial satellite 80.

In such a management system 10, it is desired to ensure the consistency of measurement information among sensors with different measurement forms.

Figure 2:
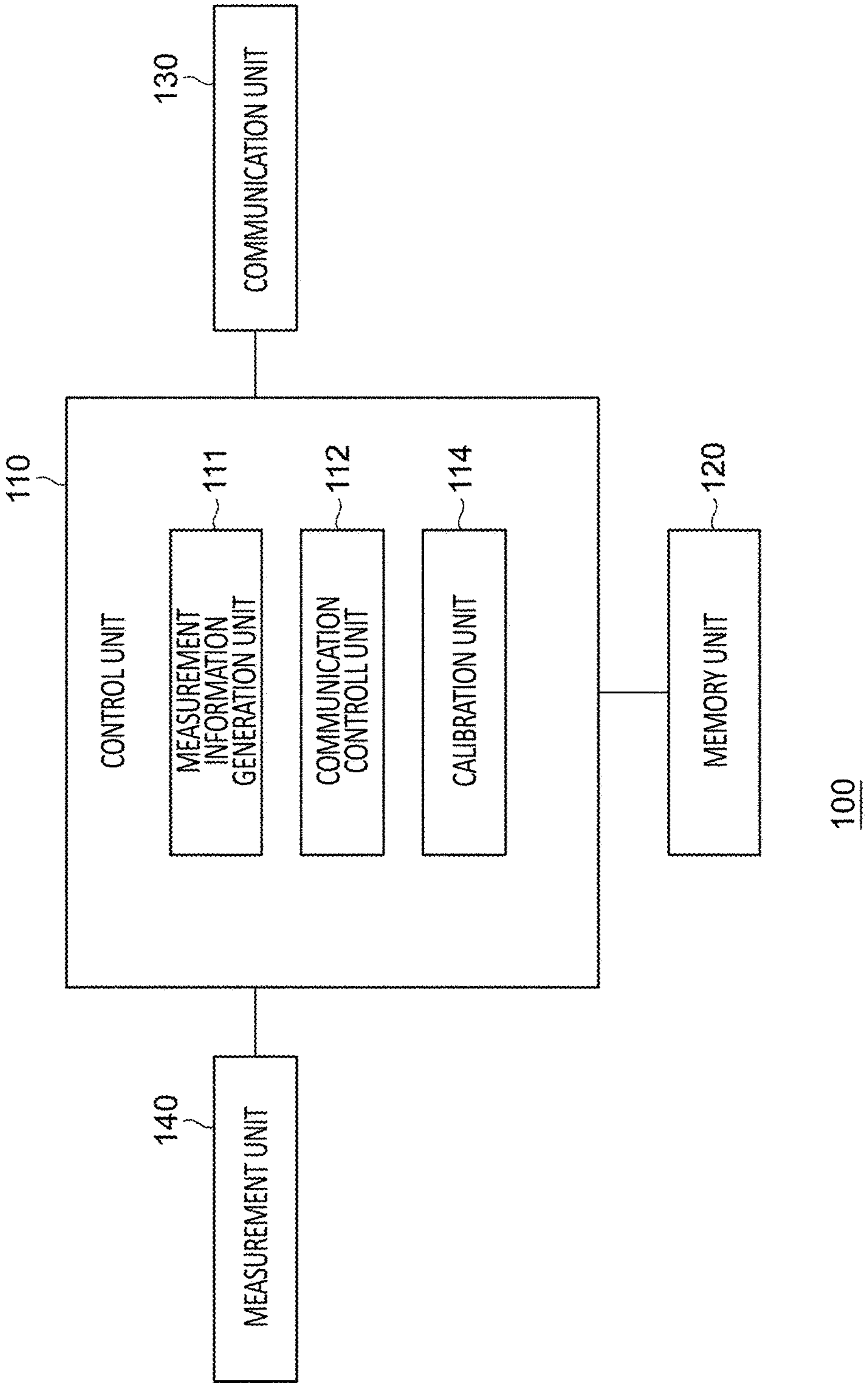
FIG. 2 shows an example of a functional block of a stationary sensor.

FIG. 2 shows an example of a functional block of the stationary sensor 100.

The stationary sensor 100 includes a control unit 110, a memory unit 120, a communication unit 130 and a measurement unit 140.

The control unit 110 may be constituted by a microprocessor such as a CPU or an MPU, a micro controller such as an MCU, or the like. The measurement unit 140 measures a physical quantity related to the environment in the area 50. The memory unit 120 stores a program or the like to achieve a process performed by the control unit 110 for the stationary sensor 100 measuring a physical quantity and sending the measurement information to the management apparatus 200. The memory unit 120 stores measurement data measured by the measurement unit 140 or measurement information based on the measurement data. The communication unit 130 includes a communication interface, and communicates to the management apparatus 200 via the network 30.

The measurement unit 140 measures a physical quantity related to the environment in the area 50 at a predetermined interval, for example, at an interval of 60 seconds for once or more. The measurement unit 140 includes a light emitting unit that emits infrared light and a light receiving unit that receives the infrared light transmitted through the gas to be measured, and may measure the gas concentration of the gas using the infrared absorption characteristics of the gas to be measured. The measurement unit 140 may measure a gas concentration of the area 50 as a physical quantity related to the environment. The measurement unit 140 may measure measurement data indicating the gas concentration of the gas leaking from the pipelines in the area 50.

The control unit 110 includes a measurement information generation unit 111 and a communication control unit 112. The measurement information generation unit 111 generates first measurement information by statistically processing the measurement data measured by the measurement unit 140. The measurement information generation unit 111 may generate statistical information including at least one of an average value, maximum value, minimum value, variance, moment, and histogram from the measurement data as the first measurement information.

The communication control unit 112 sends the first measurement information to the management apparatus 200 by controlling the communication unit 130.

The calibration unit 114 performs calibration of the stationary sensor 100. The characteristics of the stationary sensor 100 may change over time. The characteristics of the stationary sensor 100 refers to the characteristics of the optical element or the like, for example, when the stationary sensor 100 is an optical element and a gas sensor such as a $CO_2$ (carbon dioxide) sensor according to the non-dispersive infrared absorption method that measures gas concentration using infrared light. The characteristic of an optical element or the like may change over time. Therefore, the stationary sensor 100 performs calibration for the correction of the measurement precision.

The calibration unit 114 may perform calibration based on the gas concentration calculated by itself and the reference gas concentration predetermined in area 50. The calibration unit 114 may perform calibration by correcting the reference value (baseline value) of gas concentration based on the correction information provided by the management apparatus 200 described below. When the gas concentration in the area 50 meets the condition that is the reference gas concentration, the calibration unit 114 may correct the coefficient for calculating the gas concentration so that the gas concentration calculated by itself matches the reference gas concentration. The stationary sensor 100 may correct the coefficient so that the gas concentration minimum value calculated by itself within a predetermined period matches the reference value of gas concentration. The predetermined period may be a period when the gas concentration of the target gas is most likely to be the lowest. For example, it may be a period during which the operation of apparatus that may generate gas is stopped.

The memory unit 120 may be configured to store calibration information including at least one of a calibration date and time at which calibration should be performed by the calibration unit 114, a date and time of calibration performed by the calibration unit 114, a calibration method, or calibrator information. The calibration method is a method of calibration that is performed by the calibration unit 114. The calibration method may indicate, for example, that the calibration is performed during a period when the gas concentration of the target gas is most likely to be the lowest. The calibration method may indicate, for example, a period of time that takes into account weather conditions or the like that allow for performing stable measurement of the gas concentration by the stationary sensor 100.

The communication control unit 112 may send the calibration information together with the first measurement information to the management apparatus 200. The calibration method may indicate at least one of a type of gas to be measured, a concentration, a concentration score, a traceability system, a concentration accuracy, a gas component, a gas purchase date/calibration certificate issue date, a gas seller, a gas purchaser, a container symbol number, an expiration date of gas, a type of an adjustment parameter (for example, zero, span, offset, sensitivity), environment information at the time of calibration (temperature, humidity, air pressure, and date and time), or a residual pressure of calibration gas.

Figure 3:
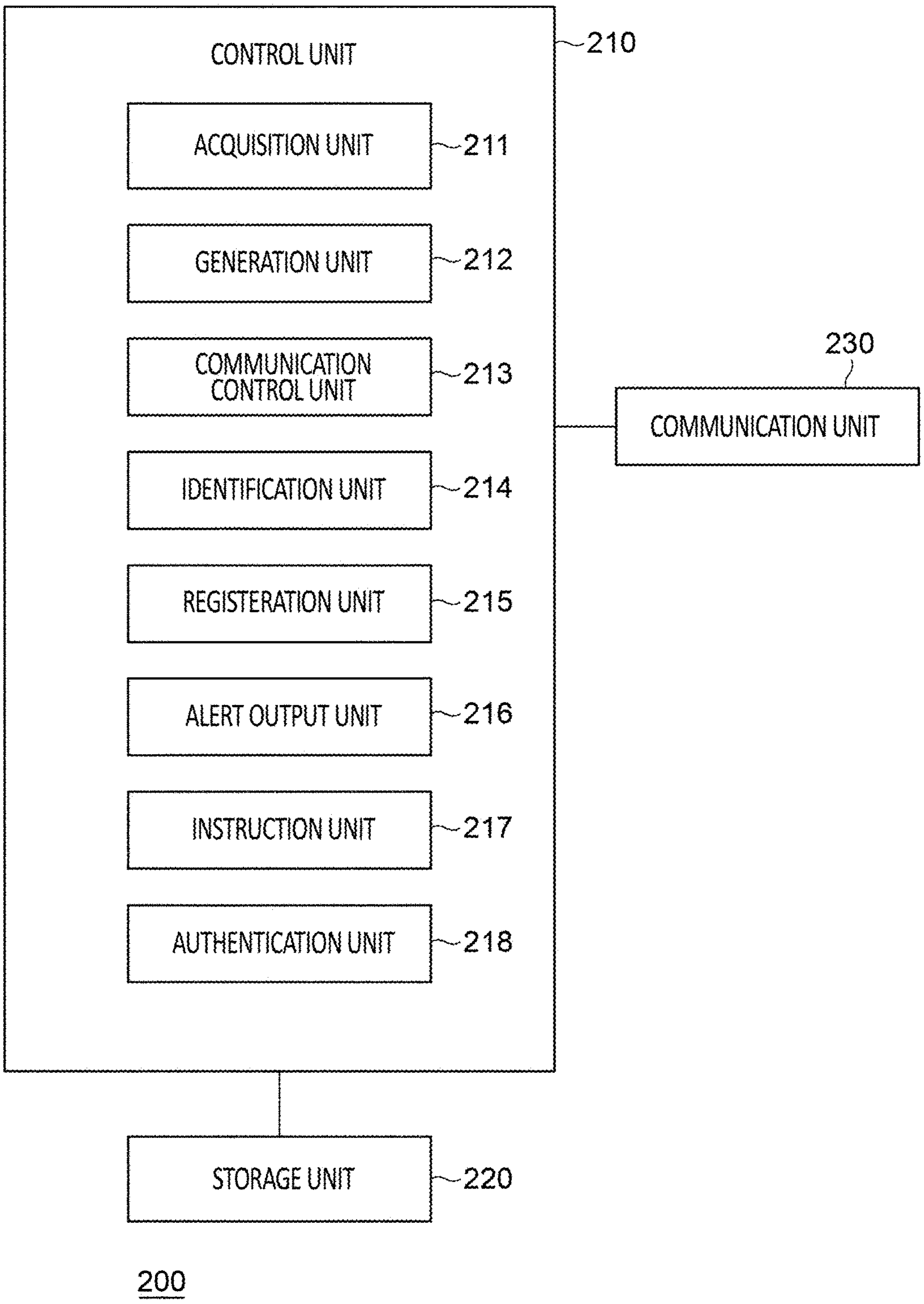
FIG. 3 shows an example of functional blocks of a management apparatus.

FIG. 3 shows an example of a functional block of the management apparatus 200. The management apparatus 200 includes a control unit 210, a storage unit 220 and a communication unit 230. The control unit 210 may be composed of a microprocessor such as a CPU or an MPU, a micro controller such as an MCU or the like. The storage unit 220 is a database that stores various measurement information collected from each stationary sensor 100, sensor 62 and sensor 82. The communication unit 230 includes a communication interface, and communicates with the stationary sensor 100 via the network 30.

The control unit 210 includes an acquisition unit 211, a generation unit 212, a communication control unit 213, an identification unit 214, a registration unit 215, an alert output unit 216, an instruction unit 217 and an authentication unit 218.

The acquisition unit 211 acquires stationary measurement information from each of the plurality of stationary sensors 100 that measures a physical quantity related to the environment in each of the plurality of areas 50. The stationary measurement information is an example of the first measurement information. Further, the acquisition unit 211 acquires, from the sensor 62 of the UAV 60, UAV measurement information indicating a physical quantity related to the environment in the plurality of areas 50 measured by the sensor 62 by movement of the UAV 60. The acquisition unit 211 acquires satellite measurement information indicating a physical quantity related to the environment in the plurality of areas 50 measured by the sensor 82 of the artificial satellite 80. The UAV measurement information and the satellite measurement information are examples of the second measurement information measured by the sensors mounted on the mobile objects. The UAV measurement information and the satellite measurement information may be distribution information indicating the distribution of the physical quantity related to the environment in the plurality of areas 50. The UAV measurement information and satellite measurement information may be, for example, distribution information indicating the distribution of the gas concentration of a particular gas in the plurality of areas 50.

The generation unit 212 generates correction information of a reference value of each of the plurality of stationary sensors 100 based on UAV measurement information or satellite measurement information. Alternatively, the generation unit 212 generates correction information of a reference value of the sensor 62 or the sensor 82 based on the plurality of stationary measurement information. The generation unit 212 identifies a minimum value of the physical quantity related to the environment from the UAV measurement information or satellite measurement information. The generation unit 212 identifies a minimum value of each piece of the stationary measurement information from the stationary measurement information of each stationary sensor 100. The minimum value of each piece of stationary measurement information is a value measured by the stationary sensor 100 during a predetermined period, during which the target physical quantity is likely to be the lowest. The stationary measurement information may attach a particular flag to its measurement value so that the measurement value of the predetermined period during which the target physical quantity is likely to be the lowest can be determined. The generation unit 212 may generate a difference between a minimum value of the physical quantity identified from the UAV measurement information or satellite measurement information and a minimum value of the physical quantity identified from the stationary measurement information, as the correction information of the stationary sensor 100, sensor 62 or sensor 82. Whether the correction information is used to calibrate either of the stationary sensor 100, sensor 62, or sensor 82 may be predetermined by the accuracy of the physical quantity measured by each sensor, depending on the characteristics of the environment in which the stationary sensor 100, sensor 62, or sensor 82 measures the physical quantity.

The generation unit 212 may determine that a sensor among the stationary sensor 100, sensor 62, or sensor 82 that has not sent measurement information together with calibration information indicating that calibration is being performed is the sensor to be calibrated and generate correction information for that sensor to be calibrated. Also, the generation unit 212 may determine the sensor to be calibrated is the lower-level sensor in the traceability system chart in the calibration information among the stationary sensor 100, sensor 62 or sensor 82, and may generate correction information for the sensor to be calibrated based on the higher-level calibration information in the traceability system chart in the calibration information.

When the calibration target is a stationary sensor 100, the communication control unit 213 sends the correction information for each of the plurality of stationary sensors 100 to each of the plurality of stationary sensors 100. When the calibration target is the sensor 62 or sensor 82, communication control unit 213 sends the correction information of the sensor 62 or sensor 82 to the sensor 62 or sensor 82.

When the acquisition unit 211 has acquired calibration information together with the UAV measurement information or satellite measurement information from the sensor 62 or sensor 82 and has not acquired calibration information from the stationary sensor 100, the generation unit 212 may generate correction information of the respective reference values of the plurality of stationary sensors 100 based on the UAV measurement information or satellite measurement information. On the other hand, when the acquisition unit 211 has acquired calibration information together with the stationary measurement information from the stationary sensor 100 and has not acquired calibration information from the sensor 62 or sensor 82, the generation unit 212 may generate correction information for the reference value of the sensor 62 or sensor 82 based on the plurality of stationary measurement information.

When the acquisition unit 211 has acquired calibration information together with the stationary measurement information from the stationary sensor 100 and has also acquired calibration information from the sensor 62 or sensor 82, the generation unit 212 may determine that the sensor with the oldest calibration date and time is the sensor to be calibrated.

The stationary sensor 100, sensor 62 or sensor 82 calibrates the reference value based on the correction information if the correction information is received from the management apparatus 200.

The identification unit 214 identifies the abnormal area, among the plurality of areas 50, where the physical quantity or the statistical information quantity shows an abnormal value, based on the UAV measurement information or satellite measurement information. In identifying the abnormal area, the historical physical quantity or statistical information quantity for the 50 plurality of areas stored in the storage unit 200 may be used. When the physical quantity based on the stationary measurement information of the stationary sensor 100 in the abnormal area, among the plurality of stationary sensors 100, does not show abnormal values, the registration unit 215 registers the identification information of the stationary sensor 100 that has provided the stationary measurement information that shows no abnormal value or UAV 60 or artificial satellite 80 in the storage unit 220. Registering may be registering identification information or abnormal values and the presence or absence of abnormalities in the storage unit 220.

When the measurement information of plurality of stationary sensors 100 and UAV measurement information or satellite measurement information in the identical area among the plurality of areas 50 diverge, the registration unit 215 registers the identification information of the stationary sensors 100 and UAV 60 or artificial satellite 80 in the storage unit 220. When the difference between the physical quantity based on the measurement information of the plurality of stationary sensors 100 and the physical quantity based on the UAV measurement information or satellite measurement information is greater than the predetermined difference, the registration unit 215 may register the identification information of the stationary sensors 100 and the UAV or satellite in the storage unit 220. More specifically, using the hoteling theory, regarding the physical quantity x obtained by the measurement information of the plurality of stationary sensors 100 and the UAV measurement information or satellite measurement information during a particular period in an identical area, when the average value of the physical quantity x is $\mu$, the standard deviation of the physical quantity x is $\sigma$, and the level of divergence $\alpha$ is $(x-\mu)^2/\sigma^2$, the identification information of the stationary sensor 100, the sensor 62, or the sensor 82 that have measured the physical quantity x may be registered in the storage unit 220 when the level of divergence $\alpha$ is equal to or greater than a particular value, and the particular value may be 9 or 36. The identical area means, for example, when at least a partial region of an abnormal area identified based on the stationary measurement information of the stationary sensor 100 and an abnormal area identified based on the UAV measurement information of the UAV 60 or the satellite measurement information of the artificial satellite 80 overlap, the abnormal areas respectively based on the stationary measurement information and the UAV measurement information or satellite measurement information may be determined to be an identical area.

For example, the stationary sensor 100 may fail to correctly measure a physical quantity related to the environment in the area 50 due to a malfunction or improper setting or the like, and abnormal values may not be able to be detected. By storing the identification information of the stationary sensor 100 that may have such a fault occurred in the storage unit 220, the faulty stationary sensor 100 can be easily known.

When the physical quantity based on the stationary measurement information of the stationary sensor 100 in the abnormal area, among the plurality of stationary sensors 100, does not show an abnormal value, the alert output unit 216 outputs an alert signal to a terminal that manages the stationary sensor 100 which has provided the stationary measurement information showing no abnormal value. The alert signal may include a message prompting inspection of the stationary sensor 100. The alert signal may include a message prompting performing calibration of the stationary sensor 100.

When the identification unit 214 identifies an abnormal area, among the plurality of areas, where the physical quantity shows an abnormal value, based on the UAV measurement information or satellite measurement information, the instruction unit 217 may instruct the stationary sensor, among the plurality of stationary sensors 100, which performs measurement at the first sampling rate within the abnormal area, to perform measurement at the second sampling rate different from the first sampling rate. The instruction unit 217 may instruct the stationary sensor, among the plurality of stationary sensors 100, which performs measurement at the first sampling rate within the abnormal area, to perform measurement at the second sampling rate that is higher than the first sampling rate. Specifically, the first sampling rate may be once per 30 seconds, and the second sampling rate may be once per 10 seconds or shorter. This allows the stationary sensor 100 installed in an area where an abnormality is likely to be occurring to measure the physical quantity related to the environment in more details than normal. Since the stationary sensor 100 only needs to increase its sampling rate during certain periods, the power consumption of the stationary sensor 100 can be suppressed.

The acquisition unit 211 may acquire, from each of the plurality of stationary sensors, statistical information acquired by statistically processing the physical quantity related to the environment in each of the plurality of areas 50, as stationary measurement information. When the identification unit 214 identifies an abnormal area, among the plurality of areas, where the physical quantity shows an abnormal value, based on the stationary measurement information, the instruction unit 217 may instruct the stationary sensor 100 in the abnormal area, among the plurality of stationary sensors 100, to send measurement information with different amount of data from the stationary measurement information that is the statistical information. When the identification unit 214 identifies an abnormal area, among the plurality of areas, where the physical quantity shows an abnormal value, based on the stationary measurement information, the instruction unit 217 may instruct the stationary sensor 100 in the abnormal area, among the plurality of stationary sensors 100, to send detailed measurement information with more amount of data than the stationary measurement information that is the statistical information. In this case, the stationary sensor 100 may send, to the management apparatus 200, the measurement information that has greater information quantity than the statistical information, such as raw data without performing statistical process, as well as at least one of the remaining battery capacity of the stationary sensor 100, the ambient temperature, humidity, air pressure, wind direction, air volume, operation time, communication history, calibration history, or maintenance history.

The identification unit 214 identifies an abnormal area, among the plurality of areas, where the physical quantity shows an abnormal value, based on the stationary measurement information of the plurality of stationary sensors 100. When the identification unit 214 has identified an abnormal area, the instruction unit 217 may instruct the sensor 62 of the UAV 60 or the sensor 82 of the artificial satellite 80 to measure the physical quantity related to the environment within the abnormal area. Further, the instruction unit 217 may instruct to send statistical information based on the UAV measurement information or satellite measurement information, or the UAV measurement information or satellite measurement information, to the UAV 60 or the artificial satellite 80.

The generation unit 212 generates macro statistical information by further statistically processing the stationary measurement information that is a plurality of pieces of statistical information from the plurality of stationary sensors 100. The generation unit 212 may generate the histogram of the physical quantity related to the environment in each area 50 as the macro statistical information, based on the plurality of pieces of stationary measurement information from the plurality of stationary sensors 100. The generation unit 212 may generate the distribution value of each of the plurality of pieces of stationary measurement information as the macro statistical information. The identification unit 214 may identify the abnormal area from the plurality of areas 50 based on the result of macro statistical process. The identification unit 214 may identify, based on a histogram or distribution value, an area 50 where the difference between the physical quantity and the physical quantity of another area 50 is equal to or greater than a threshold as an abnormal area.

The generation unit 212 may generate distribution information of the physical quantity of area 50 with each of the plurality of stationary sensors 100 existed therein, based on the stationary measurement information that is statistical information from the plurality of stationary sensors 100. The generation unit 212 may identify the position of each stationary sensor 100 by referring to a map, and generate distribution information indicating the distribution of gas concentration in a wide area including the plurality of areas 50. When generating gas concentration distribution information, the generation unit 212 may generate gas concentration distribution information, by performing data assimilation, stationary measurement information acquired from plurality of stationary sensors 100 and numerical forecast model/fluid simulation results, using a four-dimensional variational or other method. The identification unit 214 may identify, based on the distribution information, an abnormal area where an abnormality has occurred within a wide area including an area 50 with each of the plurality of stationary sensors 100 existed therein.

For example, the identification unit 214 may identify an area 50 where the physical quantity related to the environment in each area 50 is equal to or greater than a predetermined threshold as an abnormal area, based on the plurality of pieces of stationary measurement information from the stationary sensors 100 or the UAV measurement information, the satellite measurement information. For example, when a physical quantity related to the environment in each area 50 is indicating a value equal to or greater than a predetermined threshold, the identification unit 214 may estimate an amount of occurrence and location information at the occurrence source of the physical quantity, and may identify the area 50 where the location information indicates as an abnormal area, based on at least one of the plurality of pieces of stationary measurement information from the stationary sensors 100, or the UAV measurement information, the satellite measurement information.

The identification unit 214 may estimate the occurrence source of the physical quantity using, for example, an inverse analysis model that shows the relationship between the physical quantity and the occurrence source of the physical quantity related to the environment in each area 50, statistical model, atmospheric dispersion model, or machine learning model. The identification unit 214 may also estimate the occurrence source of the physical quantity using the particle-based time inverse analysis and inverse trace line analysis methods.

Time inverse analysis using the particle method may be estimating the gas leak position by calculating the behavior of particles backward in time using the particle method based on the concentration of the gas to be measured based on at least one of the first measurement information or second measurement information, and environment information including at least wind direction and wind speed.

The identification unit 214 may generate peripheral flow field and particles for at least one of the plurality of stationary sensors 100, UAV 60 and artificial satellite 80 based on environment information to estimate the historical position of the particles backward in time and estimate gas leak position. For example, the particles may be gas molecules of the gas to be measured. For example, the flow field may be a gas flow field that varies depending on wind direction and wind speed.

The identification unit 214 derives the gas concentration distribution based on, for example, environment information including at least the position of the measurement location of the gas released and diffused into the atmosphere, the gas concentration of the gas, the wind direction, and the wind speed. The identification unit 214 derives the gas concentration distribution according to the wind direction and wind speed from the gas leak position according to a computational model such as a plume model, assuming that the gas is released from a single gas leak position. The identification unit 214 estimates the gas leak position based on the gas concentration distribution derived according to the computational model and the gas concentration distribution derived based on the environment information. The identification unit 214 may estimate the assumed gas leak position at a gas concentration distribution, which is the most similar to the gas concentration distribution derived based on the environment information, among the gas concentration distributions derived according to the computational model, as the gas leak position.

When the communication control unit 213 receives calibration information together with the stationary measurement information, UAV measurement information or satellite measurement information from each sensor, the authentication unit 218 authenticates that the stationary measurement information, UAV measurement information or satellite measurement information is information related to the environment of the target area 50, based on the stationary measurement information, UAV measurement information or satellite measurement information and the calibration information. The authentication unit 218 may determine, based on the calibration information, whether the stationary measurement information, UAV measurement information or satellite measurement information is the information sent from the correctly calibrated stationary sensor 100. Authenticating may refer to ensuring that the consistency of the acquired information is high.

Also, the identification unit 214 may identify an abnormal area, among the plurality of areas 50, where the physical quantity shows an abnormal value, based on each of the stationary measurement information and the UAV measurement information or satellite measurement information. When the abnormal area identified based on the stationary measurement information by the identification unit 214 is an area identical to the abnormal area identified based on the UAV measurement information or satellite measurement information, the authentication unit 218 may authenticate that the consistency of the stationary measurement information, and the UAV measurement information or satellite measurement information is high. That is, regarding the identical area, when the identification unit 214 identifies an abnormal area based on the stationary measurement information of the stationary sensor 100 and identifies the abnormal area based on the UAV measurement information from the sensor 62 of the UAV 60 or the satellite measurement information from the sensor 82 of the artificial satellite 80, the authentication unit 218 may authenticate that the consistency of the stationary measurement information, and the UAV measurement information or satellite measurement information is high. Also, regarding the identical area, when the difference between the physical quantity based on the stationary measurement information and the physical quantity based on the UAV measurement information or satellite measurement information is within a predetermined range, the authentication unit 218 may authenticate that the consistency of the stationary measurement information, and the UAV measurement information or satellite measurement information is high. For example, regarding the identical area, when the gas outflow amount calculated based on the stationary measurement information of the stationary sensor 100 is equivalent to the gas outflow amount calculated based on the UAV measurement information from the sensor 62 of the UAV 60 or the satellite measurement information from the sensor 82 of the artificial satellite 80, the authentication unit 218 may authenticate that the consistency of the gas outflow amount information is high. Herein, equivalent refers that the error between the gas outflow amount based on the stationary measurement information and the gas outflow amount based on the UAV measurement information or satellite measurement information is ±50%, for example.

Herein, for example, authenticating refers that the authentication authority may certify that the recorded measurement information, measurement method or calculation process meets the predetermined procedures or criteria established by MMRV standards, ISO standards, legal requirements or international guidelines, etc., and that each measurement information is highly consistent. Herein, the authentication authority may be an organizational entity capable of objective evaluation of, for example, a third party organization independent of the reporting entity, a government agency, an international organization, or a particular entity or the like.

The organizational entity may, for example, inspect whether the measurement equipment or measurement method used by the reporter has sufficient accuracy or reproducibility, and the measurement equipment calibration information, measurement frequency, measurement range, data processing method, data conversion method, or uncertainty assessment is appropriate, and may authenticate the report content by the reporter. The organizational entity may, for example, issue a predetermined electronic certificate that authenticates the authenticity of the report content to at least one of the reporter or the report content. The reporter may be, for example, a gas utility that emits greenhouse gases. The report content by the reporter may be, for example, at least one of the reporter ID, date and time of report, date and time of measurement, measurement method, gas type, amount of leaked gas, leaked gas location information, and calibration information of measurement equipment.

The authentication unit 218 may convert the gas leak volume or gas leak position and operator information into a predetermined electronic report and submit it to the authentication authority. The authentication unit 218 may store at least one of the electronic report or the electronic certificate in a digital repository that can also be referenced by a third party.

Figure 4:
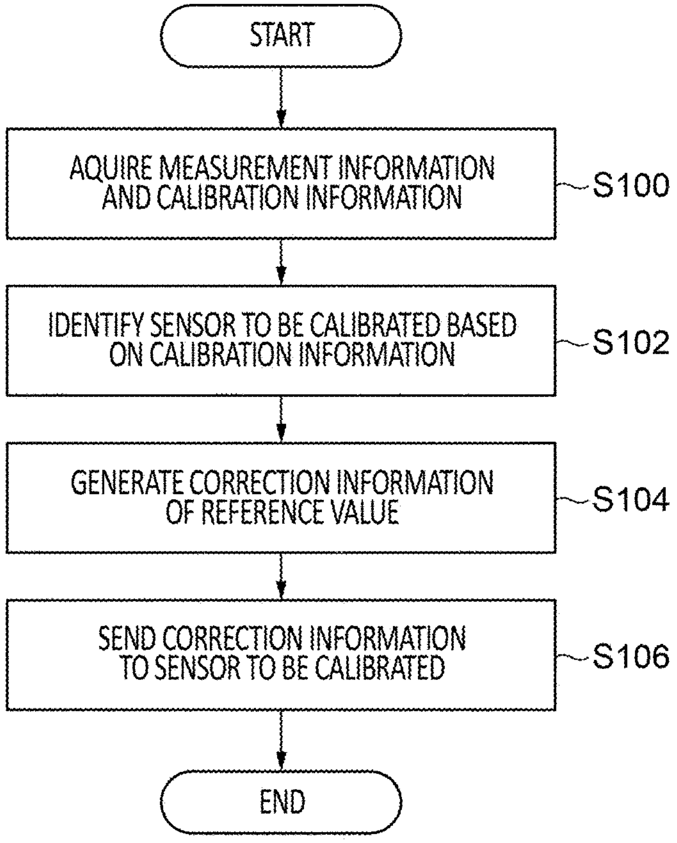
FIG. 4 is a flowchart showing an example of a procedure for sending correction information to a sensor to be calibrated.

FIG. 4 is a flowchart showing an example of sending correction information to a sensor to be calibrated.

The acquisition unit 211 acquires the calibration information together with the stationary measurement information from the stationary sensor 100. The acquisition unit 211 acquires the calibration information together with the UAV measurement information from the sensor 62. The acquisition unit 211 acquires the calibration information together with the satellite measurement information from the sensor 82 (S100).

The generation unit 212 identifies the sensor to be calibrated from the stationary sensor 100, the sensor 62 and the sensor 82 based on the respective calibration information (S102). The generation unit 212 may identify the sensor that does not provide the calibration information together with the measurement information as the sensor to be calibrated. Alternatively, the generation unit 212 may identify the sensor with a longest period from performing calibration to the current as the sensor to be calibrated.

In a case of a sensor to be calibrated being stationary sensors 100, the generation unit 212 generates correction information of a reference value of each of the plurality of stationary sensors 100 based on UAV measurement information or satellite measurement information. In a case of a sensor to be calibrated being a particular stationary sensor 100, the generation unit 212 generates correction information of a reference value of the particular stationary sensors 100 based on UAV measurement information or satellite measurement information. In a case of a sensor to be calibrated being the sensor 62 or sensor 82, the generation unit 212 generates correction information of a reference value of the sensor 62 or the sensor 82 based on the plurality of stationary measurement information (S104).

In a case of a sensor to be calibrated being stationary sensors 100, the communication control unit 213 sends the correction information for each of the plurality of stationary sensors 100 to each of the plurality of stationary sensors 100. In a case of a sensor to be calibrated being a particular stationary sensor 100, the communication control unit 213 sends the correction information for the particular stationary sensors 100 to the particular stationary sensors 100. When the calibration target is the sensor 62 or sensor 82, communication control unit 213 sends the correction information of the sensor 62 or sensor 82 to the sensor 62 or sensor 82 (S106).

The stationary sensor 100, sensor 62 or sensor 82 that has received the correction information corrects the reference value of the measurement based on the correction information.

The above process can ensure the consistency of measurement information among sensors with different measurement forms.

Figure 5:
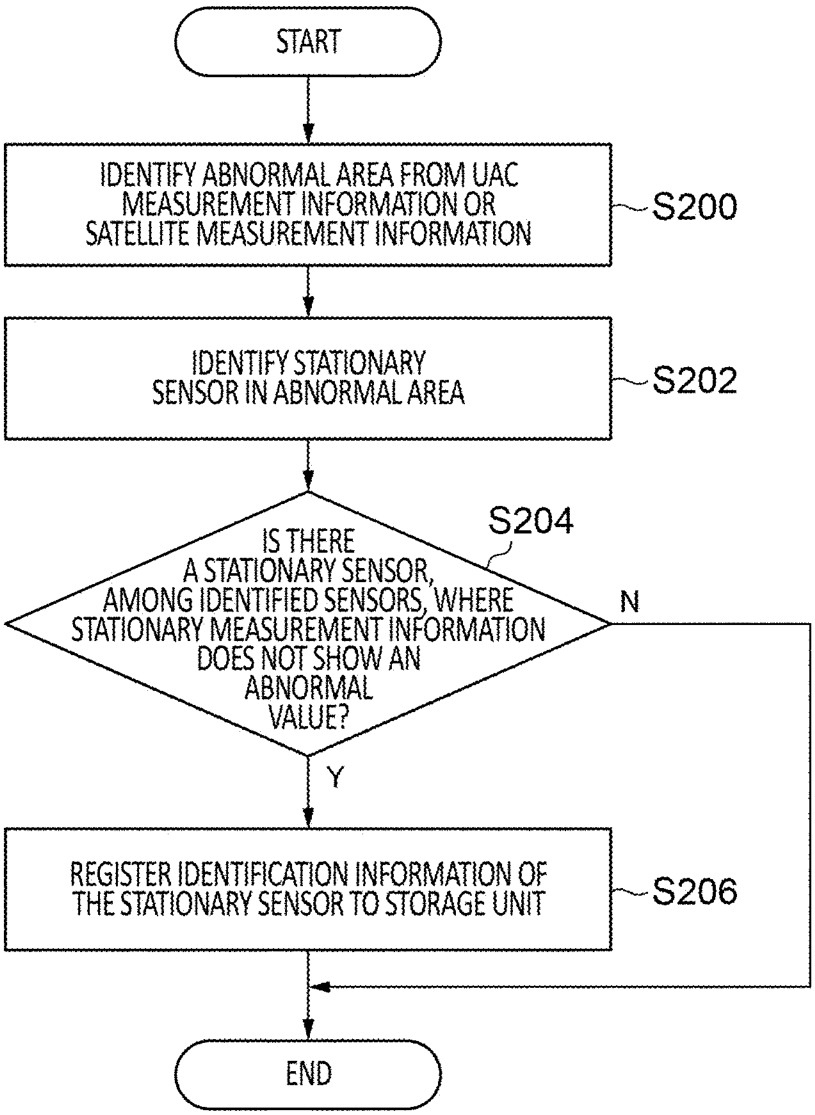
FIG. 5 is a flowchart showing an example of a procedure for registering identification information of a possibly defective stationary sensor in a storage unit.

FIG. 5 is a flowchart showing an example of registering identification information of the possibly defective stationary sensor 100 to the storage unit.

The identification unit 214 identifies the abnormal area, among the plurality of areas 50, where the physical quantity shows an abnormal value, based on the UAV measurement information or satellite measurement information (S200). The identification unit 214 identifies the stationary sensor 100 installed in the abnormal area (S202). The storage unit 220 may store the map information indicating the position of each stationary sensor. The identification unit 214 may identify the stationary sensor 100 installed in the abnormal area by referring to the map information.

The registration unit 215 determines whether the physical quantity based on the stationary measurement information of the stationary sensor 100 in an abnormal area, among the plurality of stationary sensors 100, does not show an abnormal value (S204). When the physical quantity based on the stationary measurement information of the stationary sensor 100 in the abnormal area does not show an abnormal value, the registration unit 215 registers the identification information of the stationary sensor 100 that has provided the stationary measurement information showing no abnormal value in the storage unit 220 (S206).

With the above process, by storing the identification information of the stationary sensor 100 that may have such a fault occurred in the storage unit 220, the faulty stationary sensor 100 can be easily known.

Figure 6:
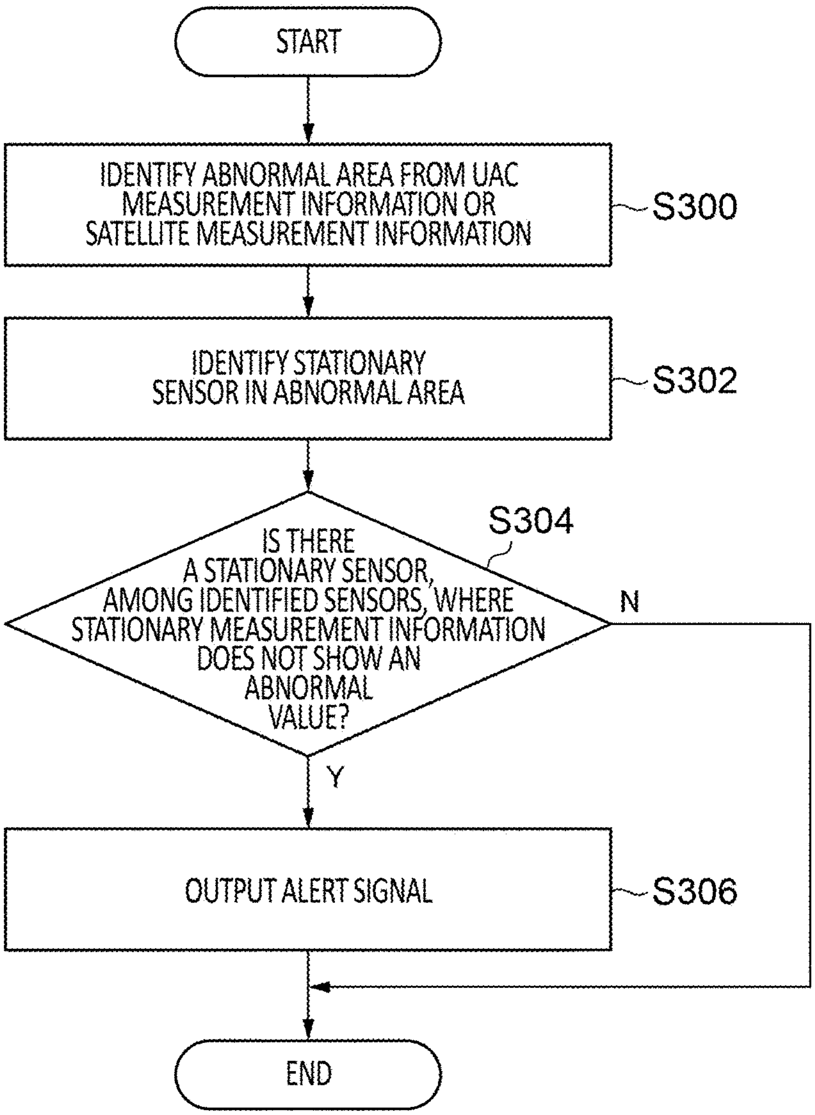
FIG. 6 is a flowchart showing an example of a procedure for outputting an alert signal when the possibly defective stationary sensor exists.

FIG. 6 is a flowchart showing an example of outputting an alert signal when a possibly defective stationary sensor 100 exists.

The identification unit 214 identifies the abnormal area, among the plurality of areas 50, where the physical quantity shows an abnormal value, based on the UAV measurement information or satellite measurement information (S300). The identification unit 214 identifies the stationary sensor 100 installed in the abnormal area (S302). The storage unit 220 may store the map information indicating the position of each stationary sensor. The identification unit 214 may identify the stationary sensor 100 installed in the abnormal area by referring to the map information.

The registration unit 215 determines whether the physical quantity based on the stationary measurement information of the stationary sensor 100 in an abnormal area, among the plurality of stationary sensors 100, does not show an abnormal value (S304). When the physical quantity based on the stationary measurement information of the stationary sensor 100 in the abnormal area does not show an abnormal value, the alert output unit 216 outputs an alert signal to a terminal that manages the stationary sensor 100 which has provided the stationary measurement information showing no abnormal value (S306).

The above process can inform the person in charge of managing the stationary sensor 100 of the stationary sensor 100 where a fault is likely to occur.

Figure 7:
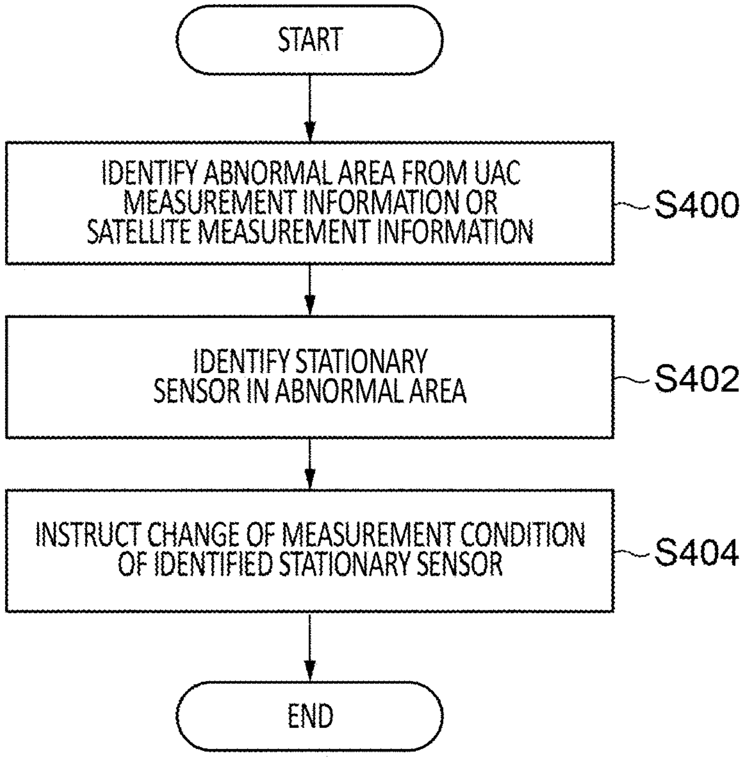
FIG. 7 is a flowchart showing an example of a procedure for changing a measurement condition of a stationary sensor installed in an abnormal area.

FIG. 7 is a flowchart showing an example of changing the measurement condition of the stationary sensor 100 installed in the abnormal area.

The identification unit 214 identifies the abnormal area, among the plurality of areas 50, where the physical quantity shows an abnormal value, based on the UAV measurement information or satellite measurement information (S400). The identification unit 214 identifies the stationary sensor 100 installed in the abnormal area (S402). The identification unit 214 may identify at least one stationary sensor 100 installed in the abnormal area.

The instruction unit 217 instructs the change of the measurement condition of the identified stationary sensor 100 to the identified stationary sensor 100 (S404). The instruction unit 217 may instruct the change of the measurement condition of the identified stationary sensor 100 to the identified stationary sensor 100 so that the measurement data is acquired in more details. The instruction unit 217 may instruct the stationary sensor 100 which performs measurement at the first sampling rate within the abnormal area, to perform measurement at the second sampling rate that is higher than the first sampling rate. Alternatively, the instruction unit 217 may instruct the stationary sensor 100 in the abnormal area to send detailed measurement information, which has a larger amount of data than the statistical information, the stationary measurement information.

This allows the stationary sensor 100 installed in an area where an abnormality may be occurring to measure physical quantities related to the environment in more detail than usual.

Figure 8:
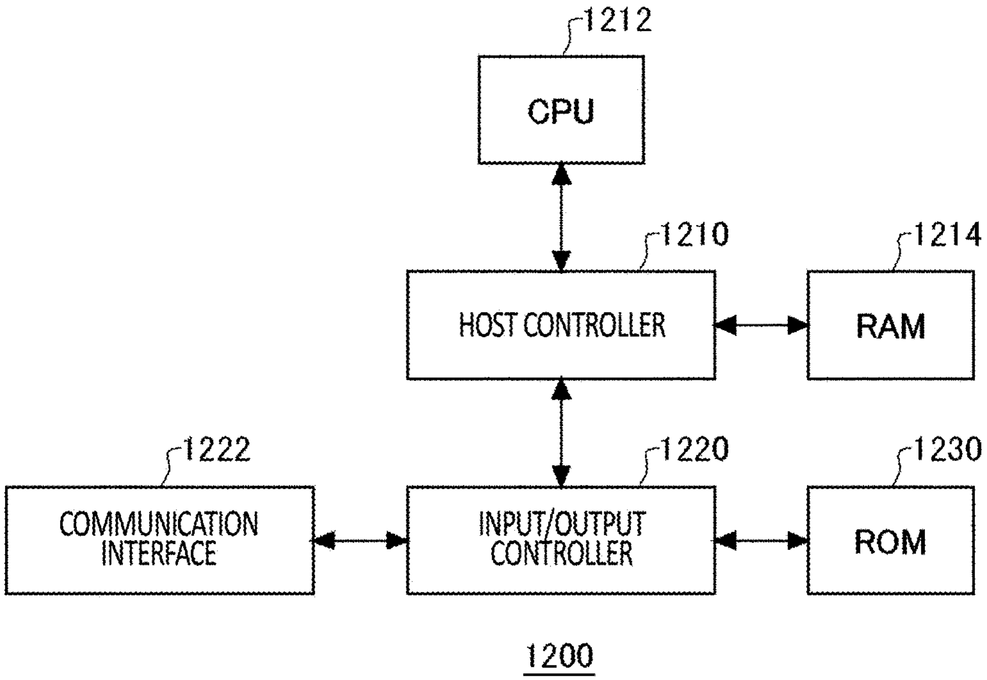
FIG. 8 shows an example of a hardware configuration.

FIG. 8 illustrates an example of a computer 1200 where a plurality of aspects of the present invention may be entirely or partially embodied. Programs installed in the computer 1200 can cause the computer 1200 to function as operations associated with the apparatus according to the embodiments of the present invention or one or more "units" of the apparatus. Alternatively, the programs can cause the computer 1200 to execute the operations or the one or more "units." The programs can cause the computer 1200 to execute a process according to the embodiments of the present invention or steps of the process. Such programs may be executed by a CPU 1212 to cause the computer 1200 to perform specific operations associated with some or all of the blocks in the flowcharts and block diagrams described in the present specification.

The computer 1200 according to the present embodiment includes the CPU 1212 and a RAM 1214, which are mutually connected by a host controller 1210. The computer 1200 also includes a communication interface 1222 and an input/output unit, which are connected to the host controller 1210 via an input/output controller 1220. The computer 1200 also includes an ROM 1230. The CPU 1212 operates according to the programs stored in the ROM 1230 and the RAM 1214, thereby controlling each unit.

The communication interface 1222 communicates with other electronic devices via a network. A hard disk drive may store the programs and data used by the CPU 1212 in the computer 1200. The ROM 1230 stores therein boot programs or the like executed by the computer 1200 at the time of activation, and/or programs depending on hardware of the computer 1200. A program is provided via a computer-readable recording medium such as a CD-ROM, a USB memory, or an IC card, or via a network. The programs are installed in the RAM 1214 or the ROM 1230 which is also an example of the computer-readable recording medium, and executed by the CPU 1212. Information processing written in these programs is read by the computer 1200, and provides cooperation between the programs and the various types of hardware resources described above. The apparatus or method may be configured by implementing operations or processing of information according to use of the computer 1200.

For example, when a communication is performed between the computer 1200 and an external device, the CPU 1212 may execute a communication program loaded in the RAM 1214 and instruct the communication interface 1222 to perform communication processing based on a process written in the communication program. The communication interface 1222, under the control of the CPU 1212, reads transmission data stored in a transmission buffer region provided in a recording medium such as the RAM 1214 or the USB memory, transmits the read transmission data to the network, or writes reception data received from the network to a reception buffer region or the like provided on the recording medium.

In addition, the CPU 1212 may cause all or a necessary part of a file or a database stored in an external recording medium such as the USB memory or the like, to be read by the RAM 1214, and execute various types of processing on the data on the RAM 1214. Next, the CPU 1212 may write the processed data back into the external recording medium.

Various types of information, such as various types of programs, data, tables, and databases, may be stored in the recording medium to undergo information processing. The CPU 1212 may execute, on the data read from the RAM 1214, various types of processing including various types of operations, information processing, conditional judgement, conditional branching, unconditional branching, information search/replacement, or the like described throughout the present disclosure and designated by instruction sequences of the programs, to write the results back to the RAM 1214. In addition, the CPU 1212 may search for information in a file, a database, or the like in the recording medium. For example, when a plurality of entries, each having an attribute value of a first attribute associated with an attribute value of a second attribute, are stored in the recording medium, the CPU 1212 may retrieve, out of the plurality of entries, an entry with the attribute value of the first attribute specified that meets a condition, read the attribute value of the second attribute stored in said entry, and thereby acquiring the attribute value of the second attribute associated with the first attribute satisfying a predetermined condition.

The programs or software modules described above may be stored in a computer-readable storage medium on or near the computer 1200. In addition, a recording medium such as a hard disk or a RAM provided in a server system connected to a dedicated communication network or the Internet can be used as the computer-readable storage medium, so that the programs are provided to the computer 1200 via the network.

Computer-readable medium may include any tangible device that can store instructions for execution by a suitable device. As a result, the computer-readable medium having instructions stored therein includes an article of manufacture including instructions which can be executed to create means for performing operations specified in the flowcharts or block diagrams. Examples of the computer-readable medium may include an electronic storage medium, a magnetic storage medium, an optical storage medium, an electromagnetic storage medium, a semiconductor storage medium, and the like. More specific examples of the computer-readable medium may include a floppy disk, a diskette, a hard disk, a random access memory (RAM), a read only memory (ROM), an erasable programmable read only memory (EPROM or a flash memory), an electrically erasable programmable read only memory (EEPROM (registered trademark)), a static random access memory (SRAM), a compact disc read only memory (CD-ROM), a digital versatile disk (DVD), a Blu-ray (registered trademark) disk, a memory stick, an integrated circuit card, and the like.

Computer-readable instructions may include either a source code or an object code written in any combination of one or more programming languages. The source code or the object code includes a conventional procedural programming language. The conventional procedural programming language may be assembler instructions, instruction-set-architecture (ISA) instructions, machine instructions, machine-dependent instructions, microcode, firmware instructions, state-setting data, or an object-oriented programming language such as Smalltalk (registered trademark), JAVA (registered trademark), C++, etc., and programming languages, such as the "C" programming language or similar programming languages. The computer readable instructions may be provided to a processor or a programmable circuit of a programmable data processing apparatus locally or via a local area network (LAN) or a wide area network (WAN) such as the Internet or the like. The processor or the programmable circuitry may execute the computer-readable instructions in order to create means for performing operations specified in the flowcharts or block diagrams.

Here, the computer may be a computer such as a personal computer (PC), a tablet computer, smartphone, a work station, a server computer, or a general purpose computer, or may be a computer system in which a plurality of computers are connected. Such computer system to which the plurality of computers are connected is also referred to as a distributed computing system, and is a computer in a broad sense. In a distributed computing system, a plurality of computers collectively execute a program by each of the plurality of computers executing a portion of the program, and passing data during the execution of the program among the computers as needed.

Examples of the processor include a computer processor, a central processing unit (CPU), a processing unit, a microprocessor, a digital signal processor, a controller, a microcontroller, and the like. The computer may include one processor or a plurality of processors. In a multi-processor system including a plurality of processors, the plurality of processors collectively execute a program by each of the processors executing a portion of the program, and passing data during the execution of the program among the processors as needed. For example, in execution of plurality of tasks, each of the plurality of processors may execute a portion of each task pieces by pieces by performing task-switching for each time slice. In this case, which portion of one program each processor is responsible for executing dynamically changes. In addition, which portion of the program each of the plurality of processors is to execute may be statically determined by multi-processor aware programming.

While the present invention has been described above with the embodiments, the technical scope of the present invention is not limited to the above-described embodiments. It is apparent to persons skilled in the art that various alterations or improvements can be made to the above-described embodiments. It is also apparent from description of the claims that the embodiments to which such changes or improvements are made may be included in the technical scope of the present invention.

Note that the order of execution of each process such as operations, procedures, steps, stages in the apparatus, system, program, and method shown in the claims, specification, and diagrams can be realized in any order as long as the order is not specifically indicated by "prior to," "before," or the like and also as long as the output from a previous process is not used in a later process. Even if the operational flow is described by using phrases such as "first" or "next" in the claims, specification, or diagrams for convenience, it does not necessarily mean that the process must be performed in this order.

(Item 1)

A management apparatus comprising:

an acquisition unit that acquires first measurement information from each of a plurality of first sensors configured to be installed in each of a plurality of areas and to measure a physical quantity related to environment in each of the plurality of areas, and acquires second measurement information from at least one second sensor configured to be mounted on at least one mobile object and to a measure physical quantity related to environment in each of the plurality of areas by movement of the at least one mobile object;

an identification unit that identifies an abnormal area, among the plurality of areas, where the physical quantity shows an abnormal value, based on each of the first measurement information and the second measurement information; and an authentication unit that authenticates that consistency between the first measurement information and the second measurement information is high when an abnormal area identified by the identification unit based on the first measurement information is an area identical to an abnormal area identified by the identification unit based on the second measurement information.

(Item 2)

The management apparatus according to item 1, further comprising a generation unit that generates correction information of a reference value of each of the plurality of first sensors based on the second measurement information, or generates correction information of a reference value of the at least one second sensor based on the first measurement information, or generates correction information of reference values of the plurality of first sensors and the at least one second sensor based on the first measurement information and the second measurement information.

(Item 3)

The management apparatus according to item 2, further comprising a communication control unit that sends the correction information each of the plurality of first sensors to each of the plurality of first sensors, or sends the correction information of the at least one second sensor to the at least one second sensor.

(Item 4)

The management apparatus according to item 2, wherein the management apparatus:

the plurality of first sensors send first calibration information including calibration date and time of performing calibration, together with the first measurement information to the management apparatus when performing calibration;

the at least one second sensor sends second calibration information including calibration date and time of performing calibration together with the second measurement information to the management apparatus when performing calibration; and the generation unit determines whether to generate correction information of the reference value of each of the plurality of first sensors, or to generate correction information of the reference value of the at least one second sensor, based on at least one of the first calibration information or the second calibration information.

(Item 5)

The management apparatus according to item 1, further comprising a registration unit that registers, to a storage unit, identification information of a first sensor that has provided the first measurement information, or identification information of a second sensor that has provided the second measurement information, when a difference between the physical quantity based on the first measurement information of each of the plurality of first sensors and the physical quantity based on the second measurement information of the at least one second sensor in an identical area of the plurality of areas, is greater than a predetermined difference.

(Item 6)

The management apparatus according to item 5, wherein regarding a physical quantity x acquired by the first measurement information of the plurality of first sensors and the second measurement information of the at least one second sensor during a predetermined period in the identical area, when an average value of the physical quantity x is set as $\mu$, a standard deviation of the physical quantity x is set as $\sigma$, and a level of divergence $\alpha$ is set as $(x-\mu)^2/\sigma^2$, and when the level of divergence $\alpha$ is equal to or greater than a particular value, the registration unit registers, to the storage unit, identification information of the first sensor or the second sensor that has measured the physical quantity x.

(Item 7)

The management apparatus according to item 1, further comprising:

an identification unit that identifies an abnormal area, among the plurality of areas, where the physical quantities shows an abnormal value, based on the first measurement information or the second measurement information; and a registration unit that registers identification information of a first sensor that has provided the first measurement information that does not show an abnormal value, or a second sensor that has provided the second measurement information, to a storage unit, when neither of the physical quantity based on the first measurement information of the first sensor in the abnormal area among the plurality of first sensors, or the physical quantities based on the second measurement information of the second sensor in the abnormal area among at least one second sensor shows an abnormal value.

(Item 8)

The management apparatus according to item 1, further comprising:

an identification unit that identifies an abnormal area among the plurality of areas, where the physical quantity shows an abnormal value, based on the first measurement information; and an instruction unit that instructs the at least one second sensor to send second measurement information of the abnormal area.

(Item 9)

The management apparatus according to item 1, further comprising an authentication unit that authenticates that consistency between the first measurement information and the second measurement information is high when a difference between a physical quantity based on the first measurement information and a physical quantity based on the second measurement information in an identical area is within a predetermined range.

(Item 10)

The management apparatus according to item 9, wherein the physical quantity is a gas outflow amount.

(Item 11)

The management apparatus according to item 7, further comprising an output unit that outputs an alert signal to a terminal that manages the first sensor which has provides the first measurement information not showing an abnormal value, when the physical quantity based on first measurement information of a first sensor in the abnormal area among the plurality of first sensors does not show an abnormal value.

(Item 12)

The management apparatus according to item 1, further comprising:

an identification unit that identifies an abnormal area, among the plurality of areas, where the physical quantities shows an abnormal value, based on the second measurement information; and an instruction unit that instructs a first sensor that performs measurement at a first sampling rate inside the abnormal area, among the plurality of first sensors, to perform measurement at a second sampling rate which is different from the first sampling rate.

(Item 13)

The management apparatus according to item 1, wherein:

the acquisition unit acquires, from each of the plurality of first sensors, statistical information acquired by statistically processing a physical quantity related to environment in each of the plurality of areas, as the first measurement information; and the management apparatus further comprises:

an identification unit that identifies an abnormal area, among the plurality of areas, where the physical quantity shows an abnormal value, based on the first measurement information; and an instruction unit that instructs a first sensor in the abnormal area, among the plurality of first sensors, to send third measurement information with an amount of data different from that of the first measurement information.

(Item 14)

The management apparatus according to item 1, wherein the at least one mobile object is at least one of an unmanned aerial vehicle or an artificial satellite.

(Item 15)

A management system, comprising:

a management apparatus according to item 1;

the plurality of first sensors; and the at least one mobile object.

(Item 16)

A management method, comprising:

acquiring, by an acquisition unit, first measurement information from each of a plurality of first sensors configured to be installed in each of a plurality of areas and to measure a physical quantity related to environment in each of the plurality of areas, and acquiring second measurement information from at least one second sensor configured to be mounted on at least one mobile object and to a measure physical quantity related to environment in each of the plurality of areas by movement of the at least one mobile object;

identifying, by an identification unit, an abnormal area, among the plurality of areas, where the physical quantity shows an abnormal value, based on each of the first measurement information and the second measurement information; and authenticating, by an authentication unit, that consistency between the first measurement information and the second measurement information is high when an abnormal area identified by the identification unit based on the first measurement information is an area identical to an abnormal area identified by the identification unit based on the second measurement information.

(Item 17)

A program, when executed by a computer, the program causing the computer to perform:

acquiring first measurement information from each of a plurality of first sensors configured to be installed in each of a plurality of areas and to measure a physical quantity related to environment in each of the plurality of areas, and acquiring second measurement information from at least one second sensor configured to be mounted on at least one mobile object and to a measure physical quantity related to environment in each of the plurality of areas by movement of the at least one mobile object;

identifying an abnormal area, among the plurality of areas, where the physical quantity shows an abnormal value, based on each of the first measurement information and the second measurement information; and authenticating that consistency between the first measurement information and the second measurement information is high when an abnormal area identified in the identifying based on the first measurement information is an area identical to an abnormal area identified in the identifying based on the second measurement information.

EXPLANATION OF REFERENCES

10: management system;

30: network; 50: area; 60: UAV; 62: sensor; 80: artificial satellite; 82: sensor; 100: stationary sensor; 110: control unit; 111: measurement information generation unit; 112: communication control unit; 114: calibration unit; 120: memory unit; 130: communication unit; 140: measurement unit; 200: management apparatus; 210: control unit; 211: acquisition unit; 212: generation unit; 213: communication control unit; 214: identification unit; 215: registration unit; 216: alert output unit; 217: instruction unit; 218: authentication unit; 220: storage unit; 230: communication unit; 1200: computer; 1210: host controller; 1212: CPU; 1214: RAM; 1220: input/output controller; 1222: communication interface; 1230: ROM.

What is claimed is:

1. A management apparatus comprising:

an acquisition unit that acquires first measurement information from each of a plurality of first sensors installed in each of a plurality of areas and to measure a gas outflow amount in each of the plurality of areas, and acquires second measurement information from at least one second sensor mounted on at least one mobile object and to measure the gas outflow amount in each of the plurality of areas by movement of the at least one mobile object;

an identification unit that identifies an abnormal area, among the plurality of areas, where the gas outflow amount shows an abnormal value, based on each of the first measurement information and the second measurement information;

an authentication unit that authenticates that consistency between the first measurement information and the second measurement information is high when an abnormal area identified by the identification unit based on the first measurement information is an area identical to an abnormal area identified by the identification unit based on the second measurement information;

a generation unit that generates correction information of a reference value of each of the plurality of first sensors based on the second measurement information, or generates correction information of a reference value of the at least one second sensor based on the first measurement information, or generates correction information of reference values of the plurality of first sensors and the at least one second sensor based on the first measurement information and the second measurement information; and an output unit that outputs an alert signal to a terminal that manages a first sensor which has provided the first measurement information not showing an abnormal value, when the gas outflow amount based on first measurement information of the first sensor in the abnormal area among the plurality of first sensors does not show an abnormal value, wherein the plurality of first sensors send first calibration information including calibration date and time of performing calibration, together with the first measurement information to the management apparatus when calibration has been performed, the at least one second sensor sends second calibration information including calibration date and time of performing calibration together with the second measurement information to the management apparatus when calibration has been performed, and the generation unit determines whether to generate correction information of the reference value of each of the plurality of first sensors, or to generate correction information of the reference value of the at least one second sensor, based on at least one of the first calibration information or the second calibration information.

2. The management apparatus according to claim 1, further comprising a communication control unit that sends the correction information each of the plurality of first sensors to each of the plurality of first sensors, or sends the correction information of the at least one second sensor to the at least one second sensor.

3. The management apparatus according to claim 1, further comprising a registration unit that registers, to a storage unit, identification information of the first sensor that has provided the first measurement information, or identification information of the at least one second sensor that has provided the second measurement information, when a difference between the gas outflow amount based on the first measurement information of each of the plurality of first sensors and the gas outflow amount based on the second measurement information of the at least one second sensor in an identical area of the plurality of areas, is greater than a predetermined difference.

4. The management apparatus according to claim 3, wherein regarding the gas outflow amount x acquired by the first measurement information of the plurality of first sensors and the second measurement information of the at least one second sensor during a predetermined period in the identical area, when an average value of the gas outflow amount x is set as $\mu$, a standard deviation of the gas outflow amount x is set as $\sigma$, and a level of divergence $\alpha$ is set as $(x-\mu)^2/\sigma^2$, and when the level of divergence $\alpha$ is equal to or greater than a particular value, the registration unit registers, to the storage unit, identification information of the first sensor or the second sensor that has measured the gas outflow amount x.

5. The management apparatus according to claim 1, further comprising: an identification unit that identifies an abnormal area, among the plurality of areas, where the gas outflow amount shows an abnormal value, based on the first measurement information or the second measurement information; and a registration unit that registers, to a storage unit, identification information of the first sensor that has provided the first measurement information that does not show an abnormal value or the at least one second sensor that has provided the second measurement information, when either of the gas outflow amount based on the first measurement information of the first sensor in the abnormal area among the plurality of first sensors, or the gas outflow amount based on the second measurement information of the second sensor in the abnormal area among at least one second sensor does not show an abnormal value.

6. The management apparatus according to claim 1, further comprising: an identification unit that identifies an abnormal area among the plurality of areas, where the gas outflow amount shows an abnormal value, based on the first measurement information; and an instruction unit that instructs the at least one second sensor to send second measurement information of the abnormal area.

7. The management apparatus according to claim 1, further comprising an authentication unit that authenticates that consistency between the first measurement information and the second measurement information is high when a difference between the gas outflow amount based on the first measurement information and the gas outflow amount based on the second measurement information in an identical area is within a predetermined range.

8. The management apparatus according to claim 1, further comprising: an identification unit that identifies an abnormal area, among the plurality of areas, where the gas outflow amount shows an abnormal value, based on the second measurement information; and an instruction unit that instructs the first sensor that performs measurement at a first sampling rate inside the abnormal area, among the plurality of first sensors, to perform measurement at a second sampling rate which is different from the first sampling rate.

9. The management apparatus according to claim 1, wherein: the acquisition unit acquires, from each of the plurality of first sensors, statistical information acquired by statistically processing the gas outflow amount in each of the plurality of areas, as the first measurement information; and the management apparatus further comprises: an identification unit that identifies an abnormal area, among the plurality of areas, where the gas outflow amount shows an abnormal value, based on the first measurement information; and an instruction unit that instructs the first sensor in the abnormal area, among the plurality of first sensors, to send third measurement information with an amount of data different from that of the first measurement information.

10. The management apparatus according to claim 1, wherein the at least one mobile object is at least one of an unmanned aerial vehicle or an artificial satellite.

11. A management system, comprising: a management apparatus according to claim 1; the plurality of first sensors; and the at least one mobile object.

12. A management method, comprising:

acquiring, by an acquisition unit, first measurement information from each of a plurality of first sensors configured to be installed in each of a plurality of areas and to measure a gas outflow amount in each of the plurality of areas, and acquiring second measurement information from at least one second sensor configured to be mounted on at least one mobile object and to measure the gas outflow amount in each of the plurality of areas by movement of the at least one mobile object;

identifying, by an identification unit, an abnormal area, among the plurality of areas, where the gas outflow amount shows an abnormal value, based on each of the first measurement information and the second measurement information;

authenticating, by an authentication unit, that consistency between the first measurement information and the second measurement information is high when an abnormal area identified by the identification unit based on the first measurement information is an area identical to an abnormal area identified by the identification unit based on the second measurement information;

a generation unit that generates correction information of a reference value of each of the plurality of first sensors based on the second measurement information, or generates correction information of a reference value of the at least one second sensor based on the first measurement information, or generates correction information of reference values of the plurality of first sensors and the at least one second sensor based on the first measurement information and the second measurement information; and an output unit that outputs an alert signal to a terminal that manages a first sensor which has provided the first measurement information not showing an abnormal value, when the gas outflow amount based on first measurement information of the first sensor in the abnormal area among the plurality of first sensors does not show an abnormal value, wherein the plurality of first sensors send first calibration information including calibration date and time of performing calibration, together with the first measurement information to the management apparatus when calibration has been performed, the at least one second sensor sends second calibration information including calibration date and time of performing calibration together with the second measurement information to the management apparatus when calibration has been performed, and the generation unit determines whether to generate correction information of the reference value of each of the plurality of first sensors, or to generate correction information of the reference value of the at least one second sensor, based on at least one of the first calibration information or the second calibration information.

13. A non-transitory computer readable medium for storing a program, when executed by a computer, the program causing the computer to perform:

acquiring first measurement information from each of a plurality of first sensors configured to be installed in each of a plurality of areas and to measure a gas outflow amount in each of the plurality of areas, and acquiring second measurement information from at least one second sensor configured to be mounted on at least one mobile object and to measure the gas outflow amount in each of the plurality of areas by movement of the at least one mobile object;

identifying an abnormal area, among the plurality of areas, where the gas outflow amount shows an abnormal value, based on each of the first measurement information and the second measurement information;

authenticating that consistency between the first measurement information and the second measurement information is high when an abnormal area identified in the identifying based on the first measurement information is an area identical to an abnormal area identified in the identifying based on the second measurement information;

a generation unit that generates correction information of a reference value of each of the plurality of first sensors based on the second measurement information, or generates correction information of a reference value of the at least one second sensor based on the first measurement information, or generates correction information of reference values of the plurality of first sensors and the at least one second sensor based on the first measurement information and the second measurement information; and an output unit that outputs an alert signal to a terminal that manages a first sensor which has provided the first measurement information not showing an abnormal value, when the gas outflow amount based on first measurement information of the first sensor in the abnormal area among the plurality of first sensors does not show an abnormal value, wherein the plurality of first sensors send first calibration information including calibration date and time of performing calibration, together with the first measurement information to the management apparatus when calibration has been performed, the at least one second sensor sends second calibration information including calibration date and time of performing calibration together with the second measurement information to the management apparatus when calibration has been performed, and the generation unit determines whether to generate correction information of the reference value of each of the plurality of first sensors, or to generate correction information of the reference value of the at least one second sensor, based on at least one of the first calibration information or the second calibration information.

* * * * *